United States Patent [19]
Poppe

[11] Patent Number: 5,573,424
[45] Date of Patent: Nov. 12, 1996

[54] APPARATUS FOR INTERFACING A BIPOLAR ELECTROSURGICAL INSTRUMENT TO A MONOPOLAR GENERATOR

[75] Inventor: R. Keith Poppe, Minneapolis, Minn.

[73] Assignee: Everest Medical Corporation, Minneapolis, Minn.

[21] Appl. No.: 386,296

[22] Filed: Feb. 9, 1995

[51] Int. Cl.⁶ .................................. H01R 29/00
[52] U.S. Cl. ........................ 439/502; 606/34; 606/42
[58] Field of Search ............................. 439/628, 638, 439/650, 651, 655, 502; 606/42, 32, 34, 37, 48, 50, 41

[56] References Cited

U.S. PATENT DOCUMENTS 4,576,144  3/1986  Ishii ............................... 439/638
5,269,780  12/1993 Roos ............................... 606/42
5,395,264  3/1995  Keith ............................. 439/502
5,472,442  12/1995 Klicek ............................ 606/42

*Primary Examiner*—Neil Abrams
*Attorney, Agent, or Firm*—Haugen and Nikolai, P.A.

[57] ABSTRACT

An adapter for interfacing a bipolar electrosurgical instrument to a monopolar electrosurgical generator comprises a pair of connectors, one having a single monopolar contact and the other having a pair of bipolar contacts is disposed between the active output terminal of the monopolar electrosurgical generator and the bipolar electrosurgical instrument. The adapter is configured to electrically connect the bipolar contacts at one end of the adapter in common with the monopolar contact at the other end. In accordance with a further embodiment, an electrical switch is provided on the electrosurgical instrument to selectively connecting both electrodes of the bipolar electrosurgical instrument to a single monopolar contact design to make with the monopolar electrosurgical generator.

3 Claims, 1 Drawing Sheet

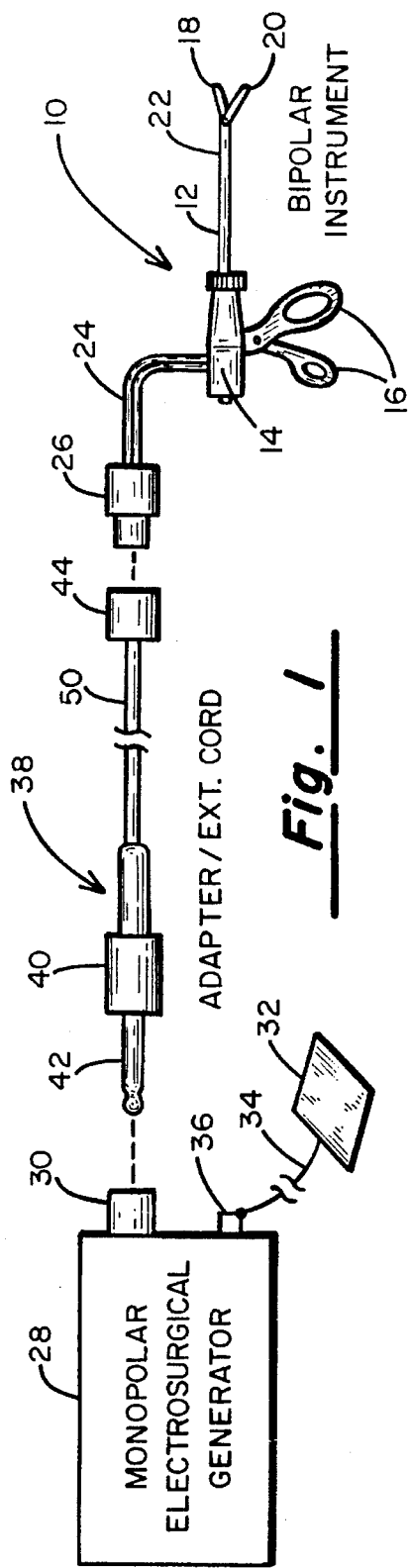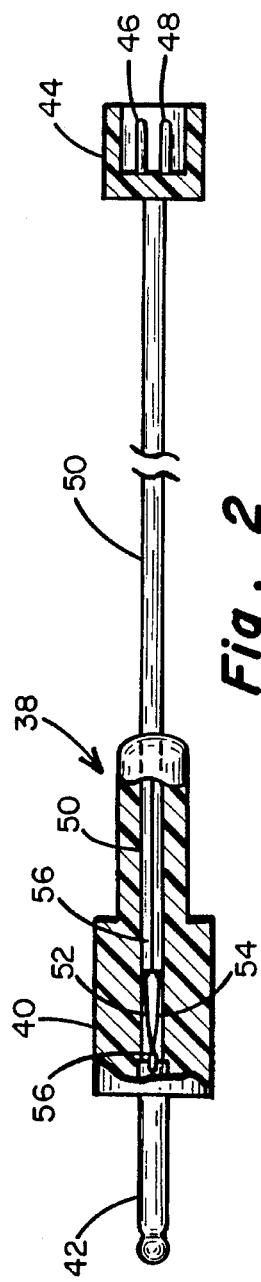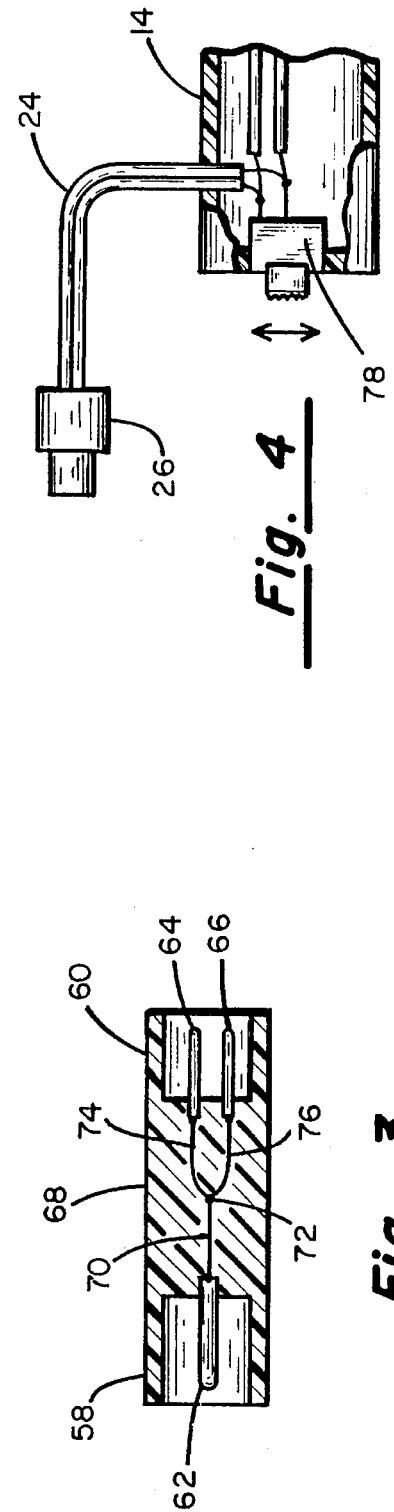

APPARATUS FOR INTERFACING A BIPOLAR ELECTROSURGICAL INSTRUMENT TO A MONOPOLAR GENERATOR

BACKGROUND OF THE INVENTION

I. Field of the Invention

This invention relates generally to apparatus used in electrosurgical procedures, and more particularly an adapter that can be used with a bipolar instrument to make it usable with a monopolar output of an electrosurgical generator as a monopolar instrument.

II. Discussion of the Prior Art

In electrosurgical procedures, a high frequency current is applied through an instrument to tissue so as to effect cutting and/or coagulation of that tissue. In the case of a monopolar system, the electrosurgical generator has a monopolar output terminal connected by a single wire to an electrode disposed on the electrosurgical instrument. The return or indifferent electrode generally comprises a skin-contacting pad affixed to the buttocks of the patient and connected by a lead to the ground or return terminal of the electrosurgical generator. In this arrangement, when the monopolar electrosurgical generator is activated, a current flows from the monopolar electrode on the instrument to the tissue being cut or coagulated and that electrical current traverses through the patient's body to the return electrode generally along a path of least resistance. In the case of a bipolar electrosurgical system, the electrosurgical instrument generally supports two closely-spaced electrodes, each of which is connected to the output terminal of the bipolar electrosurgical generator. When the two electrodes are made to contact body tissue, a current is established only in the tissue effectively bridging the two electrodes.

During the course of certain surgeries, a situation may be encountered in which the surgeon may want to convert a bipolar instrument to a monopolar instrument, recognizing that, generally speaking, monopolar electrosurgery provides electrosurgical cutting and a more global coagulation than can be attained using a bipolar instrument. Also, taking into account the fact that bipolar electrosurgical instruments are of a more recent vintage than monopolar electrosurgical instruments, there are many more monopolar electrosurgical generators in use and a manufacturer and seller of bipolar instruments may wish to offer compatibility of those instruments with monopolar electrosurgical outputs.

It is accordingly a principal object of the present invention to provide an adapter apparatus for interfacing a bipolar electrosurgical instrument to a monopolar electrosurgical output.

SUMMARY OF THE INVENTION

The foregoing object of the invention can be realized by providing an adapter module having a first connector with a monopolar contact for mating with a terminal of a monopolar electrosurgical generator, and a second connector, having a pair of bipolar contacts, for mating with a pair of conductors extending from the bipolar electrodes on the bipolar electrosurgical instrument, where the adapter further includes a means for electrically joining the monopolar contact to the pair of bipolar contacts. In accordance with a first embodiment of the invention, the means for electrically joining the monopolar contacts to each of the pair of bipolar contacts comprises a switch affixed to the bipolar electrosurgical instrument which, when closed, shorts the two bipolar electrodes together. In an alternative arrangement, the first and second connectors may be disposed on opposite ends of an extension cord and the means for electrically joining the monopolar contacts to the pair of bipolar contacts is located in one of the first and second connectors. Rather than comprising an extension cord having the first and second connectors on opposite ends thereof, it is also contemplated that the adapter may comprise the first and second connectors sharing a common housing.

DESCRIPTION OF THE DRAWINGS

The foregoing features, objects and advantages of the invention will become apparent to those skilled in the art from the following detailed description of the invention, especially when considered in conjunction with the accompanying drawings in which like numerals in the several views refer to corresponding parts.

FIG. 1 is a schematic mechanical drawing in accordance with a first embodiment of the invention;

FIG. 2 is an enlarged, partially cross-sectional view of the adapter/extension cord shown in FIG. 1;

FIG. 3 is a cross-sectional view of an alternative embodiment of the invention; and FIG. 4 is a second alternative embodiment in which an electrical switch may be used to selectively convert an electrosurgical instrument from a bipolar mode to a monopolar mode.

DESCRIPTION OF THE PREFERRED EMBODIMENT

Referring first to FIG. 1, there is indicated generally by numeral 10 a typical bipolar electrosurgical instrument, here represented by a bipolar forceps 12 designed for performing laparoscopic surgery. However, it is to be understood that the present invention may be used with a wide variety of bipolar electrosurgical instruments, including scissors, snares, scalpels, etc., and, accordingly, limitation to a forceps-style device is not intended and should not be inferred. The instrument 12 comprises a handle portion 14 having scissors-style actuating means 16 for causing the jaws 18–20 of the instrument pivotally joined to one another at the distal end of a elongated tubular barrel 22 to open and close as the scissors handles 16 are manipulated. As is conventional in bipolar instruments, the two jaws 18 and 20 comprise separate electrodes that are electrically insulated from one another and which are connected by conductors extending through the barrel 22 and the handle portion 14 to a cord 24 terminating in a bipolar female plug 26.

Identified by numeral 28 is a monopolar electrosurgical generator having an output terminal 30 in the form of a female socket that is internally connected in the generator 28 to a source of high frequency current. A return body electrode pad 32 is connected by a conductor 34 to the return terminal 36 of the electrosurgical generator.

To interface the monopolar output of electrosurgical generator 28 with the bipolar electrosurgical instrument 10, an adapter cord 38 is provided. It comprises a first connector 40 having a monopolar contact 42 (FIG. 2) for mating with the female socket 30 of the monopolar output of electrosurgical generator. At the opposite end of the adapter is a connector 44 having a pair of contacts 46 and 48 configured to mate with the female jacks in the plug 26 of the bipolar electrosurgical instrument 10. A pair of conductors extend from the bipolar terminals 46 and 48 through an insulating jacket 50. As seen in the cross-section portion of the connector 40, these two conductors 52 and 54 are connected together at a common junction 56 to which the monopolar contact 42 is also electrically joined. By interposing the adapter/extension cord shown in FIGS. 1 and 2 between the monopolar electrosurgical generator 28 and the bipolar instrument 10, the same voltage will be applied to both jaw electrodes 18 and 20, thus converting them to monopolar operation.

FIG. 3 illustrates an alternative embodiment of the adapter in accordance with the present invention. Here, the first and second connectors 58 and 60, incorporating their respective monopolar and bipolar contacts 62 and 64–66, respectively, share a common housing 68. In this arrangement, the monopolar contact 62 is connected by a conductor 70 to a junction 72 where conductors 74 and 76 are also joined. The conductors 74 and 76 connect the bipolar contacts 64 and 66 to the junction 72.

In use, the adapter of FIG. 3 can either be connected directly to the electrosurgical generator 28 by inserting the female socket 60 within the connector 58 and then using a two conductor cable (not shown) to join the other connector 60 of the adapter module to the plug 26 on the electrosurgical instrument 14. Alternatively, the adapter module of FIG. 3 may be connected directly to the plug 26 of the electrosurgical instrument and then a single insulated conductor, having appropriate plugs on opposed ends thereof, may be used to connect the monopolar contact 62 to the female jack of the monopolar electrosurgical generator 28.

Referring next to FIG. 4, a further embodiment of the invention comprises a modification to the bipolar instrument 10 wherein a single pole, single throw electrical switch 78 is mounted on the end of the handle portion 14 of the instrument and arranged such that when the switch is closed, the wires in the cable 24 leading to the two female sockets in the plug 26 become shorted together, as are the electrodes comprising the jaws 18 and 20 of the instrument. When the switch is thrown to its open position, however, the short circuit connection is removed and the instrument is again capable of operating in a bipolar mode when connected to a bipolar electrosurgical generator.

When used in a monopolar mode, however, an elongated cord having appropriate connectors at opposed ends for mating with the output terminal 30 of the monopolar generator 28 and with the plug 26 would be interposed between the items 26 and 30.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. Apparatus for interfacing a bipolar electrosurgical instrument to a monopolar electrosurgical generator comprising:
    (a) a first connector having a monopolar contact for mating with a terminal of said monopolar electrosurgical generator;
    (b) a second connector having a pair of bipolar contacts for mating with a pair of conductors extending from the bipolar electrosurgical instrument; and
    (c) means for electrically joining the monopolar contact to each of the pair of bipolar contacts.

2. The apparatus as in claim 1 wherein the first and second connectors are disposed on opposite ends of an extension cord and the means for electrically joining the monopolar contact to the pair of bipolar contacts is located in one of the first and second connectors.

3. The apparatus as in claim 1 wherein the first and second connectors share a common housing.

* * * * *